United States Patent [19]

Shlenker

[11] Patent Number: 5,045,341

[45] Date of Patent: Sep. 3, 1991

[54] COVERING SUCH AS A SUIT, GLOVE, CONDOM OR SHEATH FORMING A CHEMICAL BARRIER AGAINST HARMFUL AGENTS AND METHODS OF MAKING THE SAME

[76] Inventor: Robin R. T. Shlenker, 2165 E. Alameda Ave., Denver, Colo. 80209

[21] Appl. No.: 482,978

[22] Filed: Feb. 22, 1990

Related U.S. Application Data

[63] Continuation-in-part of Ser. No. 246,337, Sep. 19, 1988, Pat. No. 4,935,260, which is a continuation-in-part of Ser. No. 143,184, Jan. 13, 1988, Pat. No. 4,919,966, which is a continuation-in-part of Ser. No. 74,629, Jul. 17, 1987, Pat. No. 4,771,482.

[51] Int. Cl.$^5$ .................... A01N 1/02; A41D 19/00
[52] U.S. Cl. ............................ 427/2; 2/167; 2/168; 128/844; 604/349
[58] Field of Search ............... 2/159, 161 R, 167, 168; 128/844; 827/2; 604/349, 353

[56] References Cited

U.S. PATENT DOCUMENTS

| | | | |
|---|---|---|---|
| 4,545,841 | 10/1985 | Jackrel | 2/159 X |
| 4,662,006 | 5/1987 | Ross | 2/167 X |
| 4,853,978 | 8/1989 | Stockum | 604/292 X |
| 4,881,277 | 11/1989 | Hogle | 2/169 |
| 4,901,372 | 2/1990 | Pierce | 2/167 |
| 4,930,522 | 6/1990 | Busnel et al. | 128/844 |
| 4,935,308 | 6/1990 | Guema et al. | 2/159 X |

OTHER PUBLICATIONS

C. L. Fox abstracts.

*Primary Examiner*—Michael Lusignan
*Attorney, Agent, or Firm*—Robert E. Purcell

[57] ABSTRACT

A covering such as a suit, glove, condom or sheath forming a chemical barrier against harmful agents. The covering is flexible, stretchable, and relatively thin, and includes at least one relatively thin chemical barrier that will neutralize the harmful characteristics of the harmful agents. If an object cuts through the covering and into a person's skin or if a harmful agent tries to traverse through the covering, the chemical barrier will neutralize the harmful characteristics of the harmful agent so that the agent is neutralized either before reaching the person's skin, after reaching the person's skin, or both. Various methods of making the covering are also disclosed.

57 Claims, 2 Drawing Sheets

5,045,341

COVERING SUCH AS A SUIT, GLOVE, CONDOM OR SHEATH FORMING A CHEMICAL BARRIER AGAINST HARMFUL AGENTS AND METHODS OF MAKING THE SAME

BACKGROUND OF THE INVENTION

This patent application is a continuation-in-part of U.S. patent application Ser. No. 246,337, filed Sept. 19, 1988, now U.S. Pat. No. 4,935,260 for "Covering Such As A Suit, Glove, Condom Or Sheath Forming A Chemical Barrier Against Harmful Agents And Methods Of Making The Same", which is a continuation-in-part of U.S. patent application Ser. No. 143,184, filed Jan. 13, 1988, now U.S. Pat. No. 4,919,966 for "Covering Such As A Glove, Condom Or Sheath For Inhibiting The Spread Of Contagious Diseases And Methods Of Making And Using The Same", which in turn is a continuation-in-part of U.S. patent application Ser. No. 074,629, filed on July 17, 1987, for "Glove For Inhibiting The Spread Of Contagious Diseases And Method Of Using The Same", now U.S. Pat. No. 4,771,482. All of these applications are owned by the same applicant.

There are a number of contagious diseases that can be spread by passing infectious agents or microbes from one person's blood or other infective body fluid to another person's blood or other body fluid. Two of the most feared diseases that can be spread in this manner are Hepatitis and Acquired Immunodeficiency Syndrome, otherwise known as AIDS. Often, one must touch, handle or otherwise come in contact with a person's body fluid either knowing that the person has a disease such as AIDS or without an opportunity to determine adequately whether the person has such a disease. For example, doctors and nurses must treat patients and perform surgical operations on patients sometimes knowing that the person has a contagious disease or during an emergency situation when there is no opportunity to determine whether the person has such a disease. Similarly, policemen and ambulance workers must often handle and treat persons involved in automobile accidents, shootings, and the like without an opportunity for determining whether the person has a contagious disease. Also, persons may desire sexual intercourse without knowing whether their sex partner possesses a sexually transmittable disease such as AIDS.

Doctors, dentists, medical technologists, and nurses protect against the transmission of contagious diseases in the work place and during invasive procedures by wearing conventional flexible, stretchable, disposable, sterile latex gloves. Such latex gloves are sometimes powdered on the inside with talc or a similar material to help keep the glove interior dry and to facilitate removal of the glove. A decision was recently made to equip the Denver, Colo. police force with such latex gloves so that policemen could use the gloves in situations where they could contact another person's body fluids, such as at car accidents and shootings. While these conventional latex gloves provide a great degree of protection against the transmission of contagious diseases, such gloves can be torn, ripped, punctured or otherwise cut. The person's hand is often correspondingly cut immediately below the cut in the glove. For example, doctors often cut their fingers and hands with a scalpel during operations and sometimes puncture their fingers and hands with suture needles. Also, policemen might cut their hands on pieces of glass, jagged pieces of metal, and the like at car accident scenes. The frequency of such cuts is significant, and, when considering the fear of accidentally contracting diseases such as AIDS, constitutes a serious problem.

Although the use of conventional latex condoms and other condoms have been touted as a sure prevention against sexually transmitted diseases, recent newspaper articles have reported studies that seriously question the degree of such prevention, and of course, condoms that are punctured do not provide the desired degree of protection. Thus, conventional latex condoms do not provide the desired degree of protection against sexually transmitted diseases such as AIDS.

Some other recent newspaper articles have reported findings of defects in conventional latex gloves that potentially permit the ready transfer of a virus through the glove defect. These defects include lesions, holes, and pits of up to 15 microns wide and up to 30 microns deep, as well as channels up to 5 microns wide Since an AIDS virus is on the order of one-tenth micron wide, these defects in conventional latex gloves (and perhaps in conventional latex condoms) fail to provide the desired degree and confidence of protection against the transmission of diseases.

In a broader perspective, there are problems associated with protecting a person from a host of harmful organisms and materials in the environment. For example, if a person wears normal clothing and gloves while handling acid, and the acid spills upon such clothing or gloves, the acid might eat through the protective material and eventually contact the person's skin. Therefore, a broad problem exists in protecting a person against harmful organisms and materials.

SUMMARY OF THE INVENTION

The present invention relates to a covering such as a suit, glove, condom or sheath forming a chemical barrier against harmful agents. The covering is flexible, stretchable, and relatively thin, and includes at least one relatively thin chemical barrier that will neutralize the harmful characteristics of the harmful agents. If an object cuts through the covering and into a person's skin or if a harmful agent tries to traverse through the covering, the chemical barrier will neutralize the harmful characteristics of the harmful agent so that the agent is neutralized either before reaching the person's skin, after reaching the person's skin, or both. Various methods of making the covering are also disclosed.

BRIEF DESCRIPTION OF THE DRAWINGS

The invention will be described with reference to the accompanying drawings, wherein.

DESCRIPTION OF THE PREFERRED EMBODIMENT

Figures 1, 2, 3:
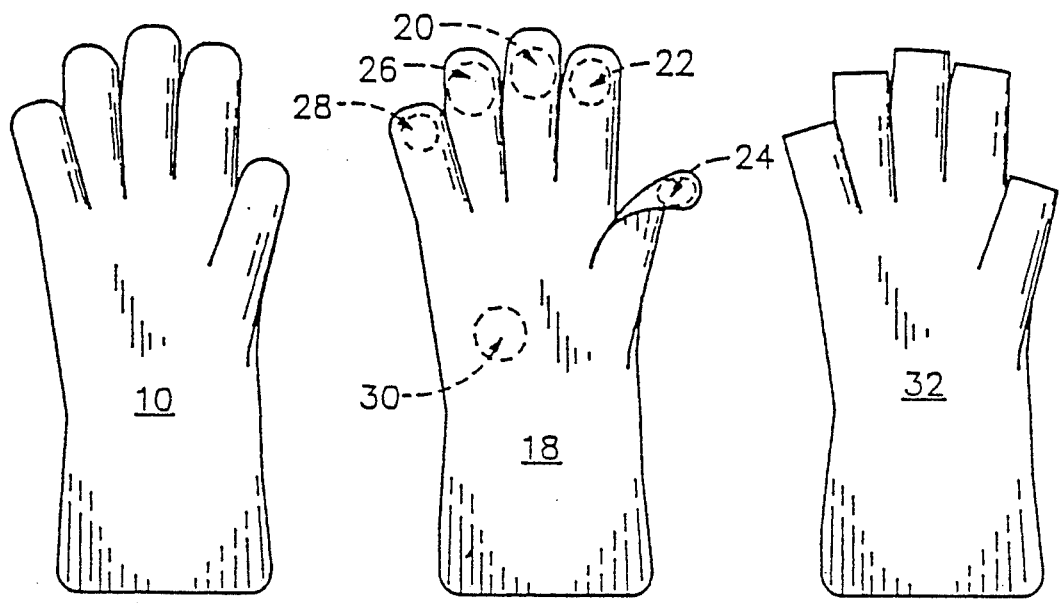
FIG. 1 is a plan view of a covering in the form of a glove in accordance with one embodiment of the present invention.
FIG. 2 is a plan view of a covering in the form of a glove according to another embodiment of the present invention depicting areas near the glove fingertips that are devoid of any chemical barrier.
FIG. 3 is a covering in the form of a glove according to yet another embodiment of the present invention in which the glove fingertips have been eliminated.

Referring now to the drawings wherein like reference numerals and symbols refer to the same item, there is shown in FIG. 1 a covering in the form of a glove 10 having a shape and configuration similar in all essential respects to the conventional latex gloves presently worn by doctors, dentists, and nurses. An example of a conventional latex glove is the "Perry" surgeon's glove manufactured by Smith & Nephew of Massillon, Ohio. According to the American Society of Testing and Materials such conventional latex gloves have a thickness normally in the range of 0.08 millimeters to 0.2 millimeters.

The glove 10 of the present invention possesses at least one pocket chamber, capsule or layer containing a chemical barrier that will neutralize the harmful characteristics of a harmful agent. In the context of the present invention, the term "harmful agent" includes broadly any substance that would be harmful to a person if the substance came into physical contact with the person. As such, the term "harmful agent" includes contagious disease producing microbes (such as viruses, bacteria and possibly spores), also includes toxins such as snake venom and PCB, and further includes hazardous substances such as pesticides and acid. In the context of the present invention, the terminology "neutralize the harmful characteristics of a harmful agent" means broadly that something changes the harmful agent so that its physical contact with a person does not harm the person, for example, to sterilize and prevent the reproduction of contagious disease producing microbes, kill such microbes, or otherwise render the microbes harmless, and for example, to chemically react with the toxins or hazardous materials so that the same are changed into a different, harmless substance (e.g., where the harmful agent is an acid, and the chemical barrier is a base). It will be appreciated that the harmful agents may be alive or not, organic or inorganic, self-mobile or non-mobile, etc.

The chemical barrier is preferably a fluid in the form of a liquid, gel, paste, or powder. Also, in certain embodiments of the present invention, the chemical barrier may be in the form of encapsulated droplets of fluid, or may be in the form of a non-rigid solid.

Figure 4:
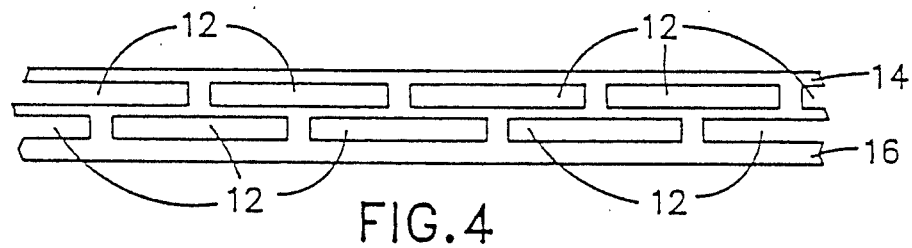
FIG. 4 is a schematic cross-sectional view of the gloves shown in FIGS. 2 and 3 revealing two layers of chambers containing a chemical barrier.
Figure 5:
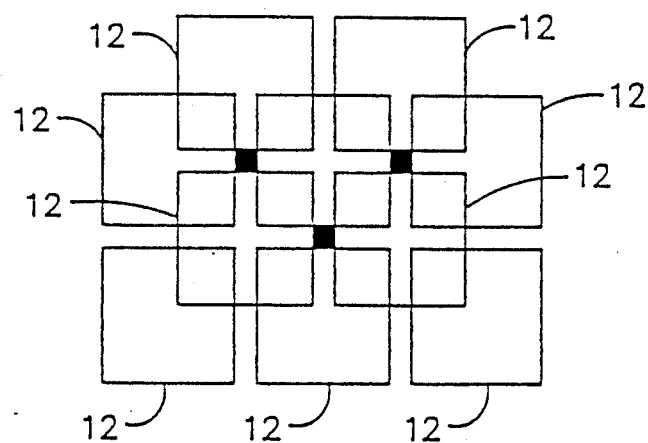
FIG. 5 is a top schematic illustration showing the staggered relation of the chambers in the two layers revealed in FIG. 4.

As best shown in FIGS. 4 and 5, the glove 10 as well as the other forms of coverings of the present invention may include an array of thin, square-shaped chambers 12 arranged side by side in two layers. The chambers 12 in each layer are staggered with respect to the chambers 12 in the adjacent layer. Such staggering minimizes the possibility that a harmful agent can traverse the covering without contacting the chemical barrier and the possibility that a needle or similar object could puncture through the glove 10 and cut the person's hand without protruding through one of the chambers 12 and releasing the chemical barrier contained therein. As shown by the darkened areas in FIG. 5, the staggered arrangement of the two layers of chambers 12 results in a relatively minuscule potential area for a needle or similar object to puncture through the glove 10 and cut the person's hand without also puncturing the cavity 12. It should be readily appreciated that either a single layer of chambers 12 could be utilized or three layers of chambers 12 arranged in a staggered relationship could be effectively used and would insure that a needle or similar object could not puncture through the glove 10 and cut a person's hand without also puncturing a chamber 12. Also, although FIGS. 4 and 5 depict relatively thin, square-shaped chambers 12, a variety of different shapes and sizes of chambers 12 can be effectively used. For example, the chambers 12 might be relatively thin and circular shaped or diamond shaped. Moreover, although FIG. 4 depicts the chambers 12 as possessing squared or cornered ends, it should be appreciated that the ends may be curved or rounded.

The thickness of the glove 10 is preferably in the range of between one-twentieth millimeter and five millimeters so that the flexibility and stretchability of the glove can be maintained. Also, the outer sheath 14 of the glove 10 (that region of the glove disposed outwardly of the outer layer of chambers 12) can be relatively thinner than the inner sheath 16 of the glove 10 (that region of the glove located inwardly of the inner layer of chambers 12). The relative thickness of the sheath 16 provides strength so that the inner sheath 16 might not be cut even though the outer sheath 14 is cut. A glove 10 constructed according to the depictions of FIGS. 4 and 5 preferably contains between 50 and 500 different chambers 12. Preferably the volume of each chamber is less than one-twentieth cubic milliliters.

Figure 6:
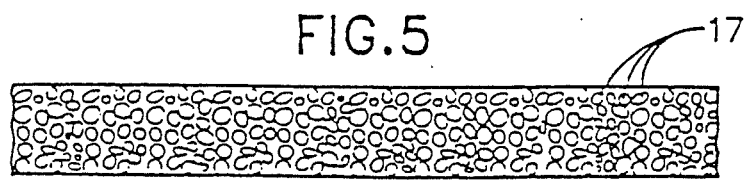
FIG. 6 is a schematic cross-sectional view of a covering according to an embodiment of the present invention.

A glove 10 as well as the other forms of coverings of the present invention can also be constructed somewhat like a sponge, with a plurality of tiny voids or chambers 17 that encapsulate the chemical barrier. Such a glove lo construction is depicted in FIG. 6. Again, it should be appreciated that it would be virtually impossible to puncture through or traverse a glove 12 constructed with a host of chambers 17 encapsulating the chemical barrier without also puncturing at least one of the chambers 17. In the embodiment depicted in FIG. 6, there are preferably at least 500 chambers 17 throughout the glove 10, and the volume of each chamber 17 is preferably less than one cubic millimeter. The sponge-like material may be sealed by causing its surfaces to melt and then hardened to form a uniform, continuous, barrier. In a variation of the embodiment depicted in FIG. 6, the sponge-like material may be saturated with the chemical barrier and then sealed on both sides with a plastic coating, a latex coating or similar coating. Such coating may be applied by dipping the saturated, sponge-like material in a vat of liquid plastic which quickly solidifies or by spraying a liquid plastic onto such material, which also quickly solidifies.

The voids or chambers 17 may be microscopic in size and may comprise pores in the glove material, such as latex. It is estimated that some of the pores that naturally form when latex is cured have a diameter or width of approximately 1 to 50 nanometers. The chemical barrier may be dispersed throughout the pores and be substantially entrapped within the pores.

The glove 18 shown in FIG. 2 may in all respects be similar to the glove 10 shown in FIG. 1 except that certain regions of the glove 18 are devoid of any chambers 12 containing the chemical barrier so that sensitivity may be maximized in those regions. Specifically, region 20 on the inside tip of the middle finger, region 22 on the inside tip of the index finger, and region 24 on the inside tip of the thumb are all devoid of chambers 12. It will be appreciated that these regions are most often used by doctors during surgery, especially for grasping a scalpel. Alternatively, regions 26, 28 on the inside tip of the ring finger and the little finger, respectively, as well as a region 30 at the heel of the hand (where the heel of a scalpel contacts the hand) may also be devoid of chambers 12 so that only a very thin layer of latex is covering those areas.

The glove 32 shown in FIG. 3 is in all respects similar to the glove 10 shown in FIG. 1 except that the fingertips and thumb tip of the glove 32 have been eliminated. The glove 32 is especially suited to be worn over a conventional latex glove. Again, the glove 32 helps maximize the sensitivity in those regions of the person's hand used to touch and feel objects.

Although the glove 10 has been described as being fashioned from latex, the present invention contemplates the glove 10 being fashioned from plastics and possibly other materials.

Figure 7:
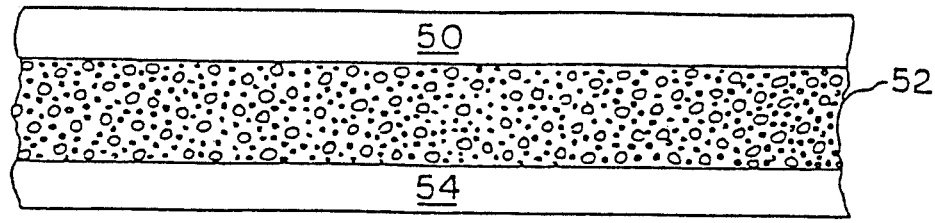
FIG. 7 is a schematic cross-sectional view of a covering according to another embodiment of the present invention.

There is shown in FIG. 7 a covering comprising an outer layer 50 of latex, plastic or other suitable material, an intermediate layer 52, and an inner layer 54, which also may be fashioned of latex, plastic or other material. The intermediate layer 52 may be formed of a material with a plurality of tiny voids or chambers, including microscopic chambers or pores, that encapsulate the chemical barrier, in all respects similar to the construction depicted in FIG. 6. The intermediate layer 52 is "sandwiched" between the outer layer 50 and the inner layer 54. It will be appreciated that the outer layer 50 and the inner layer 54 help insure that the chemical barrier does not seep from the intermediate layer 52. Also, it will be appreciated that the tiny voids or chambers within the intermediate layer 52 help insure that the chemical barrier does not significantly flow due to gravity or other forces, which would produce bulges of excessive chemical barrier as well as regions of insufficient chemical barrier. The intermediate layer 52 may be fashioned of latex having its pores substantially saturated with the chemical barrier, and the inner layer 54 and the outer layer 50 may also be formed of latex, but without the chemical barrier. In this construction, the chemical barrier is substantially prevented from migrating through the inner layer 54 and the outer layer 50 so that the chemical barrier does not contact a person's skin.

Figure 8:
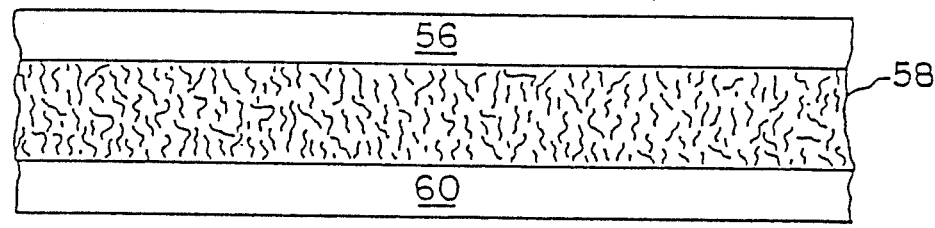
FIG. 8 is a schematic cross-sectional view of a covering according to yet another embodiment of the present invention.

There is shown in FIG. 8 another covering construction according to the present invention comprising an outer layer 56 in all respects similar to the outer layer 50 shown in FIG. 7, an intermediate layer 58, and an inner layer 60 in all respects similar to the inner layer 54 depicted in FIG. 7. The intermediate layer 58 may be formed of a variety of different materials. For example, the intermediate layer 58 may be formed of an absorbent material such as cellulose (e.g., paper), natural fiber (e.g., cotton) or synthetic fibers in either woven or unwoven condition. Also, a super absorbent material such as the materials used in baby diapers and in tampons may be used. If the chemical barrier is in fluid form, then preferably the chemical barrier substantially saturates the intermediate layer 58 and will not significantly flow in response to gravity or other forces. The intermediate layer 58 may also comprise a sponge-like material, which again can be saturated with chemical barrier in fluid form. It is also possible to intersperse metal, ceramic, or plastic fibers uniformly throughout the intermediate layer 58 for the purpose of strengthening the covering and for inhibiting the puncture and cutting of the cover. Such fibers are used in bullet proof vests. For certain functions the intermediate layer 58 or other portion of the covering may possess a screen of metal or other hard material bonded to or embedded in the covering. In yet another embodiment of the present invention, the intermediate layer may comprise a non-rigid solid such as a homogeneous copolymer containing the chemical barrier. Such a copolymer, for example, may include ion exchange resins that form the chemical barrier.

In yet another embodiment of the present invention, the intermediate layer 58 may comprise a wax or similar coating containing uniformly dispersed, encapsulated droplets of chemical barrier. Similar coatings are described in U.S. Pat. Nos. 3,079,351 and 4,112,138. In these two patents, the encapsulated droplets comprise dyes and other chemicals for creating images on paper, however, it is contemplated that the same technology may be readily adapted for use in the much different and unrelated environment of the present invention by simply substituting any one of a number of chemical barriers for the encapsulated dyes and chemicals in those two patents.

Figure 9:
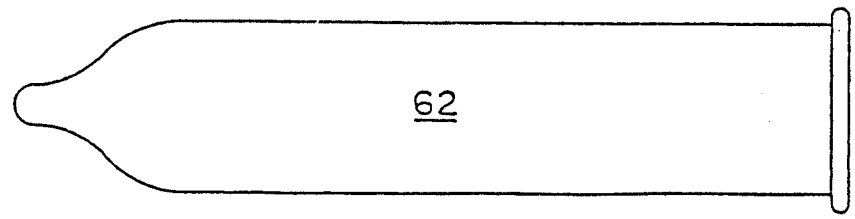
FIG. 9 is a side view of a condom according to an embodiment of the present invention.

The covering embodiments shown in FIGS. 8 and 9 may be formed by substantially saturating or coating the intermediate layer with the chemical barrier in fluid form and then forming the outer and inner layers by dipping the saturated intermediate layer in a vat of liquid plastic, latex or similar coating material which quickly solidifies or by spraying a liquid plastic, latex or similar coating material onto the saturated intermediate layer, which also quickly solidifies. The covering embodiments shown in FIGS. 8 and 9 may also be formed by first forming the inner layer (such as a latex glove), then placing the intermediate layer over the inner layer (such as by placing a conformingly shaped cotton glove saturated with the chemical barrier over the first glove), and then placing the outer layer over the intermediate layer (such as by placing another latex glove over both the cotton glove and the first latex glove).

FIG. 9 depicts a condom 62 in accordance with the present invention. The condom 62 may be constructed with the chambers depicted in FIG. 4 and 5, with the sponge-like material depicted in FIG. 6, with the "sandwiched" construction depicted in FIG. 7, or with the "sandwiched" construction shown in FIG. 8. Such construction may extend preferably throughout substantially the entire condom 62. Alternatively, such construction may comprise only the head or tip of the condom 62.

The covering and the condom shown in FIGS. 6-9 possess a thickness of preferably between one-one-thousandth millimeter and four millimeters and very preferably between one-one-hundredth millimeter and one millimeter.

The covering of the present invention may also include a dual layered suit, glove, condom or sheath formed such as by inserting one conventional latex glove within a second conventional latex glove which is of virtually identical shape and dimensions. Before the first glove is inserted into the second glove, the chemical barrier is applied over the outer surface of the first glove. Such application can be accomplished by spraying, brushing, wiping, or sprinkling the chemical barrier onto the glove, or by dipping the glove into a vat of the chemical barrier. Moreover, the chemical barrier may be in a molten state at a relatively elevated temperature when applied to the glove and then solidified in a layer around the glove. The thickness of the layer of the chemical barrier is preferably between one-one-thousandth millimeter and three millimeters and very preferably between one-one-hundredth millimeter and one-half millimeter.

The covering of the present invention may also include a dual layered suit, glove, condom, or sheath formed such as by inserting one conventional latex glove having an outer layer within a second conventional latex glove which is of virtually identical shape and dimensions. The layer coating the first latex glove may comprise a sponge-like layer or absorbent material bonded to the elastic glove such as with an adhesive. This layer includes the chemical barrier and may also include a sublayer of metal, ceramic, or plastic fibers (such as KEVLAR plastic polymer fibers made by DuPont) as previously described, or such fibers may be intermixed and uniformly dispersed within such layer.

As previously stated, the chemical barrier may be a sterilizing fluid comprising a variety of different chemicals and chemical mixtures that are effective in immediately sterilizing contagious disease producing microbes (such as viruses, bacteria and possibly spores) upon contact. In the context of the present invention, the concept of immediate sterilization means that the disease producing characteristic is rendered ineffective within ten minutes, and preferably within thirty seconds. The disease-producing characteristic can be rendered ineffective by killing the microbe, preventing reproduction of the microbe, or otherwise. In those situations where a patient or other person is known to be infected with a particular disease, the sterilizing fluid can be tailored to provide maximum effectiveness in sterilizing the microbes producing that disease. Otherwise, a more general sterilizing fluid such as a bleach solution or a detergent should be used. Also, it should be appreciated that the sterilizing fluid may be in the form of a liquid, gel, paste or powder. Care should be taken to insure that the sterilizing fluid will not react with the material from which the covering is fashioned in such a way as to cause the sterilizing fluid to leak before the covering is normally used.

Some effective sterilizing fluids are:

| Chemical Compound | Known Minimum Concentration By Volume For Immediately Sterilizing AIDS Virus (HIV-1) | Known Minimum Concentration By Volume For Immediately Sterilizing Hepatitis B Virus |
| --- | --- | --- |
| Ethyl Alcohol | 50% | 80% |
| Isopropyl Alcohol | 30% | 70% |
| NP-40 (ethylphenyl-polyethylene glycol) | 1% | — |
| Hydrogen Peroxide | 0.3% | — |
| Household Bleach | 0.1% | 10% |

The chemical barrier may be colored, especially with a color that contrasts with the color of the harmful agent or the body fluid that is likely to be contacted. So for example, if the body fluid that is likely to be contacted is blood, then the chemical barrier may be colored bright yellow or green. Also the chemical barrier may contain a fluorescent material such as those that glow in the dark. A chemical barrier with a fluorescent material would be especially advantageous for use with condoms and with gloves used by police and ambulance personnel. It is contemplated that the elastic, plastic or other material surrounding the sterilizing fluid can be sufficiently transparent or translucent to absorb any necessary electromagnetic radiation that is remitted by the fluorescent material. Also, it is contemplated that the covering could be used under the light from an ultraviolet light source so that the fluorescent material will glow immediately upon being released from or seeping through the covering.

The present invention further contemplates that the chemical barrier may possess a substance that will stain a person's skin so that if the covering is punctured completely through such as by a needle or scalpel, then the person will be alerted to such puncture (and the possibility that the person's skin is also punctured) by the stain appearing on the person's skin after the covering is removed.

The present invention has been described primarily with reference to gloves and condoms, however, it should be appreciated that a suit similar to a wet suit used by scuba divers can be used, especially when the person is handling or is exposed to toxins and hazardous material. Also, it should be appreciated that the gloves used in the present invention may extend a relatively long distance up a person's arm, and even past a person's elbow.

Although particular embodiments of the present invention have been described and illustrated herein, it should be recognized that modifications and variations may readily occur to those skilled in the art and that such modifications and variations may be made without departing from the spirit and the scope of my invention. Consequently, my invention as claimed below may be practiced otherwise than is specifically described above.

I claim:

1. A covering for forming a chemical barrier against harmful agents, and said covering possessing a first array of chambers arranged substantially side by side in a first substantially uniform layer and a second array of chambers arranged substantially side by side in a second substantially uniform layer, said first layer substantially immediately adjacent to and below said second layer, and said chambers of said first array arranged in a staggered relation relative to said chambers of said second array, said chambers containing a chemical barrier capable of neutralizing the harmful characteristics of the harmful agent.

2. A covering according to claim 1 comprising a glove.

3. A covering according to claim 1 comprising a condom.

4. A covering according to claim 1 wherein the volume of each chamber is less than substantially one-twentieth cubic milliliter.

5. A covering according to claim 1 comprising latex.

6. A covering for forming a chemical barrier against harmful agent, said covering possessing a plurality of chambers numbering at least two hundred and wherein the volume of substantially each said chamber is less than one-twentieth cubic milliliter, said chambers containing a chemical barrier capable of neutralizing the harmful characteristics of the harmful agent.

7. A covering according to claim 6 comprising a glove.

8. A covering according to claim 6 comprising a condom.

9. A covering according to claim 6 comprising latex.

10. A covering according to claim 6 wherein said chambers number at least ten thousand and each of said chambers has a diameter or width substantially in the range of between one to fifty nanometers.

11. A covering for forming a chemical barrier against harmful agents, said covering comprising a sponge-like layer of material possessing a plurality of chambers numbering at least two hundred and wherein the volume of substantially each said chamber is less than one-twentieth cubic milliliter, said chambers containing a chemical barrier capable of neutralizing the harmful characteristics of the harmful agent.

12. A covering according to claim 11 comprising a glove.

13. A covering according to claim 11 comprising a condom.

14. A covering according to claim 11 comprising latex.

15. A covering according to claim 11 wherein said chambers number at least ten thousand and each of said chambers has a diameter or width substantially in the range of between one to fifty nanometers.

16. A method of making a covering for forming a chemical barrier against harmful agents comprising the steps of:
providing a layer of sponge-like material possessing a plurality of chambers numbering at least two hundred and wherein the volume of substantially each chamber is less than one-twentieth cubic milliliter;
providing a chemical barrier capable of neutralizing the harmful characteristics of the harmful agent;
applying the chemical barrier to the sponge-like material layer such that the chemical barrier is contained within the chambers; and
sealing the surfaces of the sponge-like material layer to substantially retain the chemical barrier within the sponge-like material layer.

17. A method of making a covering according to claim 16, wherein said covering comprises a glove.

18. A method of making a covering according to claim 16, wherein said covering comprises a condom.

19. A method of making a covering according to claim 16, wherein said sponge-like material comprises latex.

20. A method of making a covering according to claim 16 wherein said chambers number at least ten thousand and each of said chambers has a diameter or width substantially in the range of between one to fifty nanometers.

21. A covering for forming a chemical barrier against harmful agents, said covering comprising an outer sheet, an intermediate layer of flexible material, and an inner sheet, a chemical barrier capable of neutralizing the harmful characteristics of the harmful agent by changing the harmful agent such that subsequent physical contact of the neutralized harmful agent with a person will not harm the person, said chemical barrier substantially dispersed within said intermediate layer, said intermediate layer disposed intermediate and adjacent to said outer sheet and said inner sheet, said outer sheet and said inner sheet adapted to substantially retain said chemical barrier within said intermediate layer.

22. A covering according to claim 21 comprising a glove.

23. A covering according to claim 21 comprising a condom.

24. A covering according to claim 21 wherein said intermediate layer comprises latex.

25. A covering according to claim 24 wherein said outer sheet and said inner sheet each comprise latex.

26. A covering according to claim 21 wherein said outer sheet and said inner sheet each comprise latex.

27. A covering according to claim 21 wherein said intermediate layer is absorbent.

28. A covering according to claim 27 wherein said intermediate layer comprises a fibrous material.

29. A method of making a covering for forming a chemical barrier against harmful agents comprising the steps of:
providing a layer of absorbent flexible material;
providing a chemical barrier capable of neutralizing the harmful characteristics of the harmful agent by changing the harmful agent such that subsequent physical contact of the neutralized harmful agent with a person will not harm the person;
inserting the chemical barrier within the absorbent flexible material layer; and
sealing the surfaces of the absorbent flexible material layer to substantially retain the chemical barrier within the absorbent material layer.

30. A method of making a covering according to claim 29 wherein said covering comprises a glove.

31. A method of making a covering according to claim 29 wherein said covering comprises a condom.

32. A method of making a covering according to claim 29 wherein said absorbent material comprises a fibrous material.

33. A method of making a multi layered covering for forming a chemical barrier against harmful agents, comprising the steps of:
providing a first flexible, stretchable layer having a thickness substantially in the range of one-one-thousandth millimeter to four millimeters;
providing a second flexible, stretchable layer having a thickness substantially in the range of one-one-thousandth millimeter to four millimeters and having a shape and configuration substantially identical to the first layer and adapted to contain the first layer conformingly therein;
providing a chemical barrier capable of neutralizing the harmful characteristics of the harmful agent by changing the harmful agent such that subsequent physical contact of the neutralized harmful agent with a person will not harm the person; and
depositing the chemical barrier such that the chemical barrier is disposed in the region between the first layer and the second layer when the first layer is conformingly contained within the second layer and such that the chemical barrier forms a substantially continuous layer having a thickness substantially in the range of one-one-thousandth millimeter to four millimeters and such that the first and second layer substantially prevent the chemical barrier from seeping out of the region and through a layer.

34. A method of making a covering according to claim 33 wherein said covering comprises a glove.

35. A method of making a covering according to claim 33 wherein said covering comprises a condom.

36. A covering for forming a chemical barrier against harmful agents comprising substantially fluid-impermeable inner and outer surface layers and an intermediate layer comprising a plurality of chambers encapsulating a chemical barrier capable of neutralizing the harmful characteristics of the harmful agent by changing the harmful agent such that subsequent physical contact of the neutralized harmful agent with a person will not harm the person.

37. A covering according to claim 36 comprising a glove.

38. A covering according to claim 36 comprising a condom.

39. A covering according to claim 36 wherein said chambers number at least ten thousand and each of said chambers has a diameter or width substantially in the range of between one to fifty nanometers.

40. A method of making a multi layered covering forming a chemical barrier against harmful agents, comprising the steps of:
providing a first flexible covering having a thickness substantially in the range of one-one-thousandth millimeter to four millimeters;
providing a second flexible covering having a thickness substantially in the range of one-one-thousandth millimeter to four millimeters and having a shape and configuration substantially identical to the first covering and adapted to contain the first covering conformingly therein;
providing a chemical barrier capable of neutralizing the harmful characteristics of the harmful agent by changing the harmful agent such that subsequent physical contact of the neutralized harmful agent with a person will not harm the person; and
depositing the chemical barrier such that the chemical barrier is disposed in the region between the first covering and the second covering when the first covering is conformingly contained within the second covering and such that the chemical barrier forms a substantially continuous layer having a thickness substantially inn the range of one-one-thousandth millimeter to three millimeters and such that the coverings substantially prevent the chemical barrier from seeping out of the region and through a covering.

41. A method of making a covering according to claim 40 wherein said multi layered covering comprises a glove.

42. A method of making a covering according to claim 40 wherein said multi layered covering comprises a condom.

43. A method of making a multi layered covering forming a chemical barrier against harmful agents, comprising the steps of:
providing a first flexible covering;
providing a second flexible covering having a shape and configuration substantially identical to the first covering and adapted to contain the first covering conformingly therein;
providing a chemical barrier capable of neutralizing the harmful characteristics of the harmful agent by changing the harmful agent such that the subsequent physical contact of the neutralized harmful agent with a person will not harm the person; and
depositing the chemical barrier such that the chemical barrier is disposed in the region between the first covering and the second covering when the first covering is conformingly contained within the second covering and such that the chemical barrier forms a substantially continuous layer having a thickness substantially in the range of one-one-thousandth millimeter to three millimeters ad such that the coverings substantially prevent the chemical barrier from seeping out of the region and through a covering.

44. A method of making a covering according to claim 43, wherein said multi layered covering comprises a glove.

45. A method of making a covering according to claim 43 wherein said multi layered covering comprises a condom.

46. A method of making a multi layered covering forming a chemical barrier against harmful agents, comprising the steps of:
providing a first flexible, stretchable covering having a thickness substantially in the range of one-one-thousandth millimeter to four millimeters;
providing a second flexible, stretchable covering having a thickness substantially in the range of one-thousandth millimeter to four millimeters and having a shape and configuration substantially identical to the first covering and adapted to contain the first covering conformingly therein;
providing a chemical barrier capable of neutralizing the harmful characteristics of the harmful agent by changing the harmful agent such that the subsequent physical contact of the neutralized harmful agent with a person will not harm the person;
depositing the chemical barrier such that the chemical barrier is deposited in a substantially continuous coating over the first covering; and
placing the first covering with the substantially continuous coating of chemical barrier into the second covering such that the chemical barrier is maintained in a substantially continuous coating between and adjacent to the first covering and the second covering.

47. A method of making a covering according to claim 46, wherein said multi layered covering comprises a glove.

48. A method of making a covering according to claim 46 wherein said multi layered covering comprises a condom.

49. A method of making a covering according to claim 46 wherein said coating is substantially uniform.

50. A covering for forming a chemicalbarrier against harmful agents, said covering comprising an outer sheet, an intermediate layer of flexible material, and an inner sheet, a chemical barrier capable of neutralizing the harmful characteristics of the harmful agent by changing the harmful agent such that subsequent physical contact of the neutralized harmfulagent with aperson willnot harm the person, a layer of fibrous materials seleced from the groupconsistnig of metal, ceramic, and plastic, said chemical barrier substantially dispersed within said intermediate layer, said intermediate layer disposed intermediate and adjacent to said outer sheet and said inner sheet, said outer sheet and said inner sheet adapted to substantially retain said chemical barrier within said intermediate layer.

51. A covering according to claim 50 wherein said fibrous layer is dispersed substantially throughout said intermediate layer.

52. A covering according to claim 51 wherein said fibrous layer is intermixed and uniformly dispersed substantially throughout said intermediate layer.

53. A covering according to claim 50 comprising a glove.

54. A covering according to claim 50 comprising a condom.

55. A covering according to claim 50 wherein said intermediate layer comprises latex.

56. A covering according to claim 55 wherein said outer sheet and said inner sheet each comprise latex.

57. A covering according to claim 50 wherein said outer sheet and said inner sheet each comprise latex.

* * * * *